(12) United States Patent
Sun (10) Patent No.: US 7,285,279 B2
(45) Date of Patent: Oct. 23, 2007

(54) METHOD OF TREATING MALIGNANCIES AND VIRAL INFECTIONS AND IMPROVING IMMUNE FUNCTION WITH A DIETARY SUPPLEMENT

(75) Inventor: Alexander Sun, Milford, CT (US)

(73) Assignee: Sun Farm Corporation, Milford, CT (US)

( * ) Notice: Subject to any disclaimer, the term of this patent is extended or adjusted under 35 U.S.C. 154(b) by 0 days.

(21) Appl. No.: 10/448,147

(22) Filed: May 28, 2003

(65) Prior Publication Data

US 2003/0206923 A1    Nov. 6, 2003

Related U.S. Application Data

(60) Division of application No. 10/043,485, filed on Jan. 10, 2002, now abandoned, which is a continuation of application No. 09/350,758, filed on Jul. 9, 1999, now abandoned.

(51) Int. Cl.
*A61K 36/288* (2006.01)
*A61K 36/232* (2006.01)
*A61K 36/734* (2006.01)
*A61K 36/8962* (2006.01)

(52) U.S. Cl. ............... 424/195.15; 424/757; 424/727; 424/754; 424/756; 424/765; 424/764

(58) Field of Classification Search ........... 424/195.15, 424/725, 728, 756, 757, 754
See application file for complete search history.

(56) References Cited

U.S. PATENT DOCUMENTS

| | | | |
|---|---|---|---|
| 4,465,696 A | | 8/1984 | Strahl |
| 4,613,591 A | * | 9/1986 | Aburada et al. |
| 4,839,290 A | * | 6/1989 | Kaieda et al. |
| 4,843,067 A | | 6/1989 | Liu |
| 5,053,386 A | | 10/1991 | Tung |
| 5,093,122 A | * | 3/1992 | Kodera |
| 5,302,699 A | | 4/1994 | Kawamura et al. |
| 5,437,866 A | * | 8/1995 | Sun |
| 5,714,464 A | | 2/1998 | Piraino et al. |
| 5,770,217 A | | 6/1998 | Kutilek, III et al. |
| 6,168,795 B1 | * | 1/2001 | DJang |
| 6,241,995 B1 | * | 6/2001 | Estrada et al. |

FOREIGN PATENT DOCUMENTS

| | | |
|---|---|---|
| EP | 0 382 551 | 8/1990 |
| JP | 58072523 | 4/1983 |
| JP | 01100126 A | 4/1989 |
| JP | 5213765 | 8/1993 |
| JP | 06014794 A | 1/1994 |
| JP | 07173070 A | 7/1995 |
| JP | 08291078 A | 11/1996 |
| KR | 9210762 B | 12/1992 |
| WO | WO91/06307 | 5/1991 |
| WO | WO-99/06057 | 2/1999 |

OTHER PUBLICATIONS

CN 1097289, 1997—English abstract (XP 002152085).*
Derwent English abstract of CN 1135335 A, 1996.*
Derwent English abstract of RU 2075313 C1, 1997.*
Derwent English abstract of CN 1194857 A, 1998.*
Derwent English abstract of CN 1183908 A, 1998.*
Derwent English abstract of JP 56010117 A, 1981.*
Derwent English abstract of JP 02256621 A, 1990.*
Database WPI, Section Ch, Week 199719, Derwent Publications Ltd., London, GB; AN 1997-204055 XP002152085 & CN 1 097 289A (abstract).
Feher et al., Immunopharmacology and Immunotoxicology (1989) 11(1):55-61.
Lewis et al., Medical Botany, Plants Affecting Man's Health, John Wiley & Sons, Inc. (1977) pp. 96-101.
Translation of Notice of Preliminary Rejection for Korean Application No. 10-2002-7000342, mailed on Jun. 26, 2006, 3 pages.
Database WPI, Derwent, accession No. 1997-204055.
Database WPI, Derwent, accession No. 1996-461342.
Hayashi et al., Planta Medica (1997) 63(2):102-105.
Ikekawa et al., Cancer Research (1969) 29:734-735.
Lohr, Abstracts of the Annual Meeting of the American Society for Microbiology (1988) 88(316):316.
Partial European Search Report for EP 05076615.3, mailed on Feb. 24, 2006, 6 pages.

* cited by examiner

*Primary Examiner*—Susan Coe Hoffman
(74) *Attorney, Agent, or Firm*—Morrison & Foerster LLP (57) ABSTRACT

A dietary supplement comprising as its active ingredients soybean, mushroom and mung bean is used in a method to in a method to ameliorate at least one effective malignancy or viral infection or to enhance immune functions. The active components of the dietary supplement include phytoestrogens, β-glucans, saponins, inositol hexaphosphate, and lectins.

9 Claims, 6 Drawing Sheets

METHOD OF TREATING MALIGNANCIES AND VIRAL INFECTIONS AND IMPROVING IMMUNE FUNCTION WITH A DIETARY SUPPLEMENT

This patent application is a division of claims priority to U.S. application Ser. No. 10/043,485 filed 10 Jan. 2002, now abandoned, which is a continuation of U.S. application Ser. No. 09/350,758, filed 09 Jul. 1999, now abandoned, both of which are incorporated herein by reference.

TECHNICAL FIELD

This invention relates to treatments effective in treating malignancies and restoring $CD4^+$ cell levels, and also to dietary supplements that improve immune functions. In particular, it concerns compositions that are derived from plants, foods and extracts thereof, that are used in a particular combination as dietary supplements, which are effective against malignancies and depressed immune functions and which improve overall immune function.

BACKGROUND OF THE INVENTION

Nutritional support for cancer patients has been studied extensively. It provided a substantial improvement in nutritional status of cancer patients whose malnutrition was due to reduced oral intake, but it fell short of its goals when the malnutrition was due to malignancy. No improvement in the tumor's response to therapy has been demonstrated by this approach, which primarily manipulated protein and caloric intake in a generic strategy.

In the past three decades, studies have repeatedly shown that some foods contain components with antitumor or immune-enhancing activities. These components are non-toxic and have different modes of action, and their individual antitumor activities are modest. A partial list of these components is presented in Table 1. The use of fruits and vegetables, which were not specifically selected for their antitumor attributes and may contain only a few of these components, for cancer prevention has been recommended by the American Cancer Society and the National Cancer Institute; their increased consumption is considered a major cause for the reduction in cancer-related deaths in recent years.

TABLE 1

Non-toxic Antitumor Components in Plants[1]

| Antitumor Components | Functions |
| --- | --- |
| Protease inhibitors in soybean | Suppress chemically induced carcinogenesis in colon, anal gland, oral cavity, lung, breast, and skin |
| Autoclave-resistant factor in soybean | Protection against metastasis of radiation-induced thymic lymphosarcoma and weight loss |
| Plant sterols | Protective effect against tumorigenesis in colonic mucosa |
| Saponin (found in soybeans) | Potentiation of rabies vaccine in mice<br>Antitumor activity<br>Inhibition of induction of Epstein-Barr virus |
| Genistein (found in soybeans) | Inhibits angiogenesis and growth of human prostate cancer |
| Biochanin A (found in soybeans & mung beans) | Inhibits human prostate cancer |
| Other isoflavones | Inhibit growth of human cancer cell lines derived from gastrointestinal tract |
| Inositol hexaphosphate (found in soybeans or mung bean) | Enhances NK cell activity and suppresses tumor growth<br>Suppresses tumor formation and growth<br>Inhibits growth of human leukemia cells and induces differentiation of K-562 cells |
| β-Glucans (e.g., lentinan) (found in mushrooms) | Host-dependent inhibition of sarcoma 180 cell growth<br>Immunoaccelerators, immunopotentiators, and immunomodulators<br>Enhance production of IL-1, TNF, LAK activity, cytotoxic T lymphocytes, cytotoxic peritoneal exudate cells |
| Lectins (found in mung beans) | Selective stimulation of T lymphocyte proliferation |

[1]Abbreviations are as follows:
NK, natural killer;
IL-1, interleukin-1;
TNF, tumor necrosis factor;
LAK, lymphokime-activated killer.

Non-small cell lung cancer (NSCLC) causes the death of >400,000 patients annually in the United States and Europe. The benefit of conventional therapies for unresectable stage IIIB and IV NSCLC patients is marginal; the generally accepted median survival time (MST) of stage IV patients has remained 4-6 months for the control group and 6-10 months for the treatment group, and the one-year survival time is usually only 20%. Even stage I NSCLC patients have a 52% death rate due to lung cancer within two years when treated with radiotherapy alone. Clearly, more effective therapies are needed.

With regard to AIDS patients, improvement in $CD4^+$ cell count has become a major area of research in AIDS therapies. Current therapies can not increase $CD4^+$ counts to normal range in the 12-month treatment period. Many patients are still dying from depressed immune functions even when their serum HIV load can be reduced to an undetectable level by antiretroviral therapy.

Continuous treatment with toxic antiretroviral drugs for a long period of time has generated instances of intolerable toxicity; many patients cannot continue these highly toxic treatments. Therefore, it would be useful to the industry to provide non-toxic treatments that are effective against malignancies and viral infections.

DISCLOSURE OF THE INVENTION

The invention is directed to a dietary supplement and a protocol of administration that is used to treat malignancies and viral infections and to otherwise improve overall immune function. The dietary supplement is a selected vegetable (SV) composition that is a freeze-dried commercial vegetable soup prepared by Sun Farm Corporation (Milford, Conn.). It is a brown powder with a slightly sweet taste. The ingredients of SV include soybean, mushroom, mung bean, red date, scallion, garlic, lentil bean, leek, hawthorn fruit, onion, ginseng, angelica root, licorice, dandelion root, senegal root, ginger, olive, sesame seed, and parsley. Rather than focusing on a single immune modulator, SV is a combination of various kinds of herbs and vegetables selected for their specific activities. Thus, immune function may be augmented in a concerted effort.

MODES OF CARRYING OUT THE INVENTION

The combination of SV as further described contains soybean, mushroom, and mung bean as the active components. The remainder of the components, red date, scallion, garlic, lentil bean, leek, hawthorn fruit, onion, ginseng, angelica root, licorice, dandelion root, senegal root, ginger, olive, sesame seed, and parsley are added for flavor. The main active components of soybean, mushroom and mung bean, are genestein, biochanin A, coumestrol, inositol hexaphosphate, β-glucans, and lectins.

Vegetables and herbs were selected for inclusion in SV on the basis of two criteria: absence of toxicity and presence of one or more known antitumor or immune-enhancing components as found in Table 1.

One embodiment of the invention is a method to ameliorate at least one effect of malignancy or viral infection comprising administering to a subject in need of such treatment an effective amount of the dietary supplement comprising soybean, shiitake mushroom, and mung bean, wherein the composition is administered periodically for a time to achieve amelioration.

Another embodiment of the invention is a method of enhancing immune functions comprising administering to a subject an effective amount of a dietary supplement comprising soybean, shiitake mushroom and mung bean periodically for a time to achieve enhanced immune functions.

Anti-viral effects such as increasing $CD4^+$ cell levels, have been found in patients from HIV, Epstein-barr virus, herpes, and influenza viruses. In addition, malignancies such as small cell lung cancer, non-small cell lung cancer, prostate cancer, breast cancer, stomach cancer, small intestine cancer, colonrectal cancer, renal cell carcinoma, soft tissue sarcoma, ovarian cancer, thyroid cancer, acrcinoid tumors, sarcoma of the bone, melanoma, glioblastoma, oligodendroglioma, astrocytoma, medulloblastoma, acute lymphomas, chronic leukemias, cancer of unknown primary site, Hodgkin's disease, and non-Hodgkin's disease have been successfully treated with an administration of the dietary supplement in accordance with the invention. Moreover, as this dietary supplement is non-toxic and has immune enhancing properties, it can be used to prevent immunosuppressing diseases.

In general, the amounts of material administered are in the range of those corresponding to 25-200 gms. of the soybean, shiitake mushroom, and mung bean components and similar amounts of the optional additives.

The dietary supplement can be in the form of a freeze-dried product or extracts of the essential components along with the flavorings. The freeze-dried material or extracts can be added to water or other soup and administered orally on a regular basis. SV can be boiled with water or soup and frozen for convenience and then heated for use. About 10-50 mg per 50 kg body weight of the freeze dried or net weight SV is preferable and about 30 mg per 50 kg body weight is more preferable. Thus, about 100-500 mg of about a 10% SV mixture with a liquid per 50 kg body weight is preferable and about 300 mg is more preferable. Preferably, the dietary supplement should be administered once or twice daily. Administration of 3 to 4 times a week is also acceptable.

In another embodiment, the present invention is directed to the daily ingestion of nontoxic vegetables and herbs containing known antitumor components that can improve clinical outcomes of patients who already have advanced tumors. These observations suggest the benefits of SV and led to the present invention.

Various species of mushroom can be used in the regimen of the invention. Acceptable species include: *Polyponis frondosus; Polyporus giganteus; Polyporus umbellatus; Trametes cinnabarina*. However, the following are more preferable: *Armillariella mellea; Armillariella tabescens; Clitocybe nebularis; Lentinus lepideus* Fr.; *Panus rudis* Fr.; *Pleurotus spodolencus* Fr.; *Pholiota adiposa; Boletus erythropus*; and *Gyroporus castaneus*. More preferred are: *Flammulina velutipes; Lepista luscina* (Fr) Sing.; *Lepista nuda* (Bull. ex. Fr.); *Oudemansiella radicata; Tricholompsis platyphylla; Panellus stypticus; Pleurotus ostreatus; Schizophyllum commune* Fr.; *Tricholoma gambosum, Agaricus arvensis; Coprinus atramentarius; Coprinus comatus; Agrocybe paludosa; Agrocybe praecox; Pholiota lubrica; Pholiota nameko; Rozites caperata; Cortinarius bovinus* Fr.; *Cortinarius salor* Fr.; *Cortinarius violaceus; Gymnopilis liquiritae; Rhodophyllus clypeatus; Rhodophyllus sinuatus; Boletus edulis* Bull.; *Boletus pulvertlentus; Boletus regius* Krombh.; *Boletus rubellus* Krombh.; *Suillus aeruginascens; Suillus bovinus; Suillus liteus; Lactarius hygrophoroides; Lactarius volemus* Fr.; *Russula adusta* Fr.; *Russula crustosa; Russula delica* Fr.; and *Russula lepida* Fr. Especially preferred are: *Lentinus edodes; Panus conchatus; Tricholoma*

*matsutake*; *Tricholoma monolicum* Imai; *Agaricus bisporus*; *Agaricus campestris*; *Cortinarius cinnamomeus* Fr.; *Cortinarius collinitus* Fr.; *Cortinarius elatior* Fr.; *Cortinarius latus* Fr.; and *Lactarius hatsudake*.

A table of the properties of the various species follows:

| Species Name | Edible | Percent Inhibition of Tumor Growth |
| --- | --- | --- |
| *Polyporus frondosus* | yes | 98% |
| *Polyporus giganteus* | yes | 90% |
| *Polyporus umbellatus* | yes | 70% |
| *Trametes cinnabarina* | yes | 90% |
| *Armillariella mellea* | yes | 80% cure ophthalmocopia |
| *Armillariella tabescens* | yes | 70% |
| *Clitocybe nebularis* | yes | 80% |
| *Flammulina velutipes* | good | 80–100% |
| *Lentinus edodes* | excellent | 80–97% |
| *Lentinus lepideus* Fr. | ywa | 50–70% |
| *Lepista luscina* (Fr.) Sing. | delicious | yes |
| *Lepista nuda* (Bull.) ex. Fr.) | yes | 90–100% |
| *Oudemansiella radicata* | | |
| *Tricholomopsis platyphylla* | yes | 80–90% |
| *Panellus stypticus* | yes | 70–80% |
| *Panus conchatus* | yes | 100% |
| *Panus rudis* Fr. | yes | 70% |
| *Pleurotus ostreatus* | yes | 80% |
| *Pleurotus spodolencus* Fr. | yes | 72% |
| *Schizophyllum commune* Fr. | yes | 100% |
| *Tricholoma gambosum* | yes | 70–90% |
| *Tricholoma matsutake* | excellent | 70–100% |
| *Tricholoma mongolicum* Imai | excellent | 70–100% |
| *Agaricus arvensis* | yes | 100% |
| *Agaricus bisporus* | excellent | 100% |
| *Agaricus campestris* | excellent | 100% |
| *Coprinus atramentarius* | yes | 100% |
| *Coprinus comatus* | yes | 100% |
| *Agrocybe paludosa* | yes | 100% |
| *Agrocybe praecox* | yes | 100% |
| *Pholiota adiposa* | yes | 70–90% |
| *Pholiota lubrica* | yes | 100% |
| *Pholiota nameko* | yes | 100% |
| *Rozites caperata* | yes | 70% |
| *Cortinarius bovinus* Fr. | yes | 90% |
| *Cortinarius collinitus* Fr. | yes | 100% |
| *Cortinarius elatior* Fr. | yes | 80% |
| *Cortinarius latus* Fr. | yes | 100% |
| *Cortinarius salor* Fr. | yes | 90% |
| *Cortinarius violaceus* | yes | 100% |
| *Gymnopilus liquiritae* | yes | 90% |
| *Rhodophyllus clypeatus* | yes | 100% |
| *Rhodophyllus sinuatus* | yes | 100% |
| *Boletus edulis* Bull, | yes | 90–100% |
| *Boletus erythropus* | ? | 100% |
| *Boletus pulverulentus* | yes | 90% |
| *Boletus regius* Krombh. | yes | 90% |
| *Boletus rubellus* Krombh. | yes | 90% |
| *Gyroporus castaneus* | yes | 80% |
| *Suillus aeruginascens* | yes | 100% |
| *Suillus bovinus* | yes | 100% |
| *Suillus luteus* | yes | 90% |
| *Lactarius hatsudake* | yes | 100% |
| *Lactarius hygrophoroides* | yes | 70% |
| *Lactarius volemus* Fr. | yes | 90% |
| *Russula adusta* Fr. | yes | 80% |
| *Russula crustosa* | yes | 70% |
| *Russula delica* Fr. | yes | 100% |
| *Russula lepida* Fr. | yes | 100% |

The active components in the SV comprise phytoestrogens, β-glucans, saponin, inositol hexaphosphate, and lectins. Phytoestrogens such as genistein, coumestrol, daidzein, and biochanin A are each present in the SV based on daily oral consumption of about 1 mg-5 g/100 kg of body weight. β-glucans such as lentinan, pachymaran, zymosan, schizophyllan, KS-2, and pachyman are each present in SV based on a daily oral consumption in an amount of about 1 mg-5 g/1100 kg of body weight. Saponins and inositol hexaphosphate are each present in the SV based on daily oral consumption of about 1 mg-5 g/100 kg of body weight. Lectins, such as phytohemagglutinin and concanavalin A are each present in the SV based on daily oral consumption of from about 1 mg-5 g/100 kg of body weight.

The following examples serve to illustrate, but not to limit, the invention.

The first example that follows illustrates the influence of selected vegetables (SV) that contain known antitumor components on the survival of stage III-IV non-small cell lung cancer (NSCLC) patients. All patients were treated with conventional therapies. SV was added to the daily diet of 5 stage I patients in the toxicity study group (TG) and 6 stage III and IV patients in the treatment group (SVG), but not to the diet of 13 stage III and IV patients in the control group (CG). Age, Karnofsky performance status (KPS), and body mass index of SVG and CG patients were comparable at entry. KPS declined in the CG patients (79±8 to 55±11) but improved in the SVG patients (75±8 to 80±13) one to three months after entry. Weight change in the CG, SVG, and TG patients was −12±5%, −2±2%, and +4±4%, respectively. The median survival time and mean survival of the CG patients were 4 and 4.8 months, but in the SVG patients they were 15.5 and 15 months (p<0.01). No clinical signs of toxicity were found in the TG patients in the 24-month study period. Adding SV to the daily diet of NSCLC patients was found to be nontoxic and associated with improved weight maintenance, KPS, and survival of stage III and IV NSCLC patients.

EXAMPLE 1

Pilot Study of a Selected Vegetable Diet in Tumor Bearing Mice and Stage IIIB and IV Non-Small Cell Lung Cancer Patients.

Method

SV Preparation. SV was prepared by Sun Farm Corporation, Milford, Conn., employing "The Good Manufacturing Practices" designed to guarantee minimal contamination with heavy metals and bacteria (U.S. Federal Code of Regulations, Title 21, Part 100-69. 1996; U.S. Government Printing Office, Washington, D.C.). The ingredients of SV include: soybean, mushroom, mung bean, red date, scallion, garlic, lentil bean, leek, Hawthorn fruit, onion, ginseng, angelica root, licorice, dandelion root, senegal root, ginger, olive, sesame seed, and parsley. The mixture was boiled and then stored frozen at −20° C. and thawed at room temperature before use.

Nutritional Data and Toxicity. Random samples of SV were sent to Northeast Laboratory, Berlin, Conn., for analysis of nutritional value, heavy metals, and bacteria.

Phytoestrogens: The assay was modified from Franke et al. (Franke A A, Custer L J, Cema C M, Narala K K. Quantitation of phytoestrogens in legumes by HPLC. J. Agric Food Chem 1994; 42: 1905-13). One gram of freeze-dried SV (DSV) was dispersed in a 50 ml mixture of HCl/ethanol/butylated hydroxytoluene (10/40/0.25, v/v/v), refluxed for 2 h, filtered, and 5 µl of the filtrate was analyzed with HPLC (Nova-Pak 150 mm×3.9 mm reverse phase C18 column, Waters, Milford, Mass.). The column was eluted with a gradient from 5% to 50% acetonitrile in acetic acid-water (1/9, v/v) in 15 min at 1 ml/min followed with 7.5 min wash with 50% acetonitrile in the same buffer. Molar extinction coefficients (daidzein, 20,893 at 250 nm; genistein, 37,154 at 263 nm, coumestrol, 22,300 at 339 nm) were used for quantitative determination.

Inositol: DSV (5 g) was incubated with 10 ml of 0.33N HCl for 2 h, filtered, and diluted with deionized water (1:1, v/v). Inositol hexaphosphate was determined according to Ellis et al. (Ellis R. Morris E R, and Philpot C. Quantitative determination of phytate in the presence of high inorganic phosphate. Anal Biochem 1977; 77:536-9.)

Mouse Lung Tumor Model: Four week-old BALB/c male mice were divided into groups of 5 (Experiment I) or 8 (Experiment II) mice. Mice in each group were fed one food preparation a week prior to tumor inoculation and during the entire study period.

BALB/c Line 1 Lung tumor cells ($10^4$ cells; viability over 90%) were injected subcutaneously in the right thigh. Tumor size was measured every 2-4 days. Experiment I: Food #1 was made from Lab Chow powder, mixed with water, made into pellets, and air-dried. Food #2, #3, and #4 were made as above and mixed with a hot water extract of mung bean (#2: 10% by wt; Lab Chow, 90%), shiitake mushroom (#3: Lentinus edodes, 10% by wt), or both at the same concentrations (#4). Experiment II: Lab Chow powder (#5, Control) was mixed with freeze-dried SV (DSV) powder (#6: 5% wt/wt). Food consumption per group was measured weekly.

Clinical Study Design. Sixteen patients with knowledge of the lead cases requested SV as a nutritional supplement and volunteered their participation. The study period was 60 months from February, 1992 to January, 1997. Patients were treated with conventional therapies selected by their physicians and added SV to their daily diet. Their clinical status was monitored by their physicians and verified by the authors. Only 14 stage IIIB and IV patients who ingested SV daily for 2 months or longer were included in the study group. Karnofsky performance status (KPS) was recorded before the use of SV and 5 months later. The four patients who ingested SV less than 2 months were excluded from analyses. Patients #1 and #2 provided retrospective data; they were excluded from the statistical analyses.

Diagnosis, Staging, and Survival Time. All the patients were diagnosed in their local hospitals. The pathological slides were reviewed by the pathologist (TMF) and radiographs by the radiologists (YPH and HCY). Staging was determined according to the revised International System for Staging Lung Cancer. The survival time was calculated from the date of diagnosis of stage IIIB or IV NSCLC to the date of death or to the cut-off date.

Ingestion of SV. SV is a grayish green paste with a slightly sweet taste. It was ingested daily (approximately 283 g) by patients as part of breakfast or lunch either directly, or mixed with other foods.

Materials: All chemicals were reagent grade. Genistein, daidzein, inositol, inositol hexaphosphate, butylated hydroxytoluene, and O-toluidine were obtained from Sigma Aldrich Chemical Co. (St. Louis, Mo.), coumestrol, acetonitrile, acetic acid, trichloroacetic acid, and thiourea from Fisher Scientific (Pittsburgh, Pa.). Purina Lab Chow powder from Purina Mills (Richmond, Ind.), BALB/c mice from Charles River Laboratories (Wilmington, Mass.), and SV from Sun Farm Corporation (Milford, Conn.).

Informed Consent: All patients were informed of the ingredients in SV and that these ingredients have been used widely as foods or food flavors. They used SV daily as a food supplement, and gave written permission to the authors to review their medical records.

Results

Nutritional Value and Hazardous Contaminants of SV. The daily dose of SV contains a net wet weight of 283 grams; physiological fuel calories, 87+3; protein, 10+2 g; carbohydrate, 11+2 g; total fat, <1 mg; cholesterol, <1 mg; dietary fiber, 12+1 g; vitamin C<0.1 mg; vitamin A, <15 IU; thiamine, <4 mg; riboflavin, 45+4 mg; sodium, 45+4 mg; calcium, 9+1 mg; potassium, <1 mg; iron, <5 mg. Heavy metal content and culture plate counts of samples of SV were: arsenic <1 (PPM); cadmium, <1.3; barium, <1; chromium, <2.7; lead, <1.7; mercury, <0.1; silver, <1.3; yeast and mold count (per gram), <10; *E. coli*, <1; and standard plate count, <10. These levels are well below allowable levels.

Antitumor Components in SV: The following components were measured in SV (mg/283 g SV/daily dosage): inositol hexaphosphate, 63+6; genistein, 2.6+0.1; daidzein, 4.4+0.1; coumestrol, 15.5+0.4.

Figure 1A:
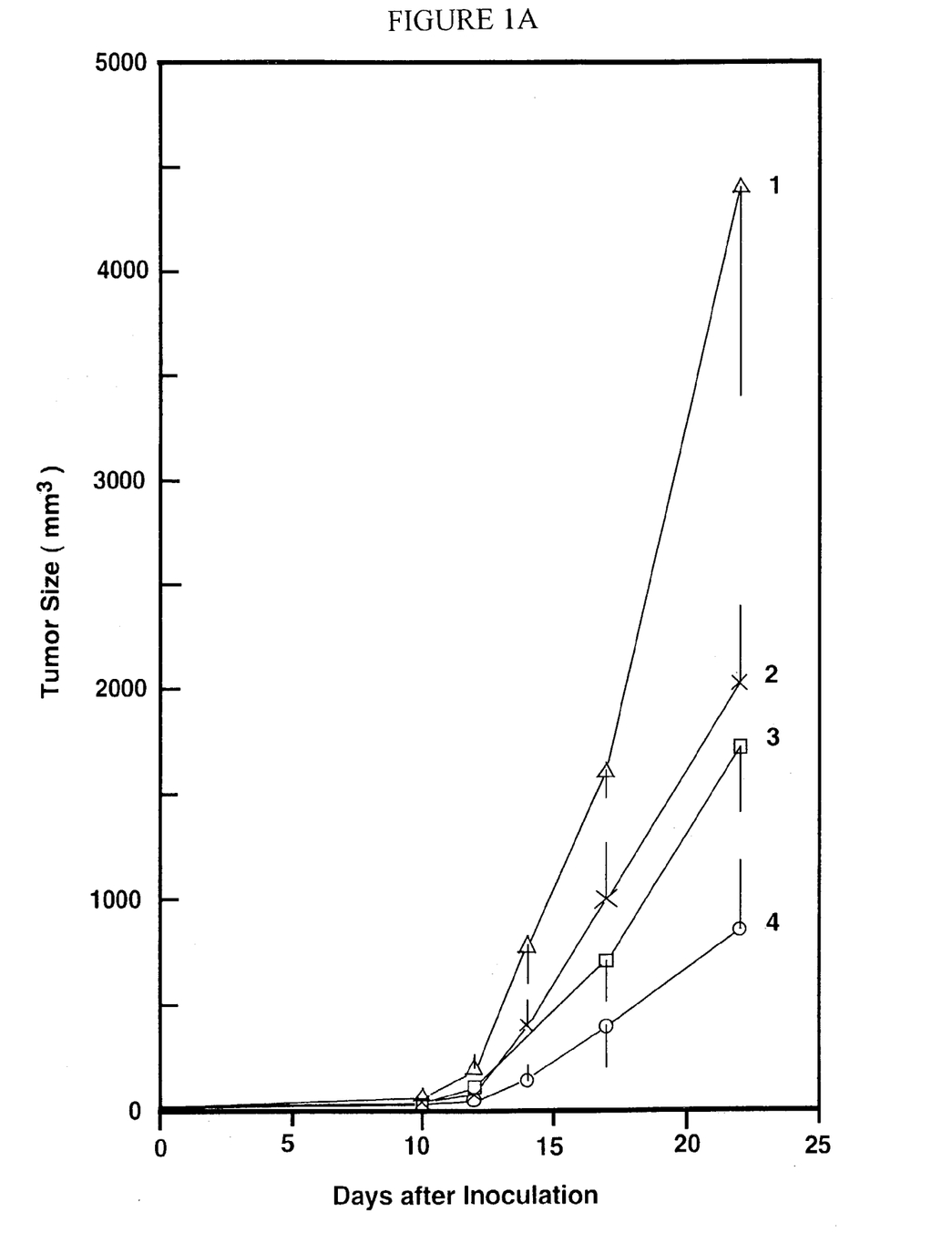
FIGS. 1a and 1b are graphs illustrating the growth of lung tumors in BALB/c mice.
Figure 1B:
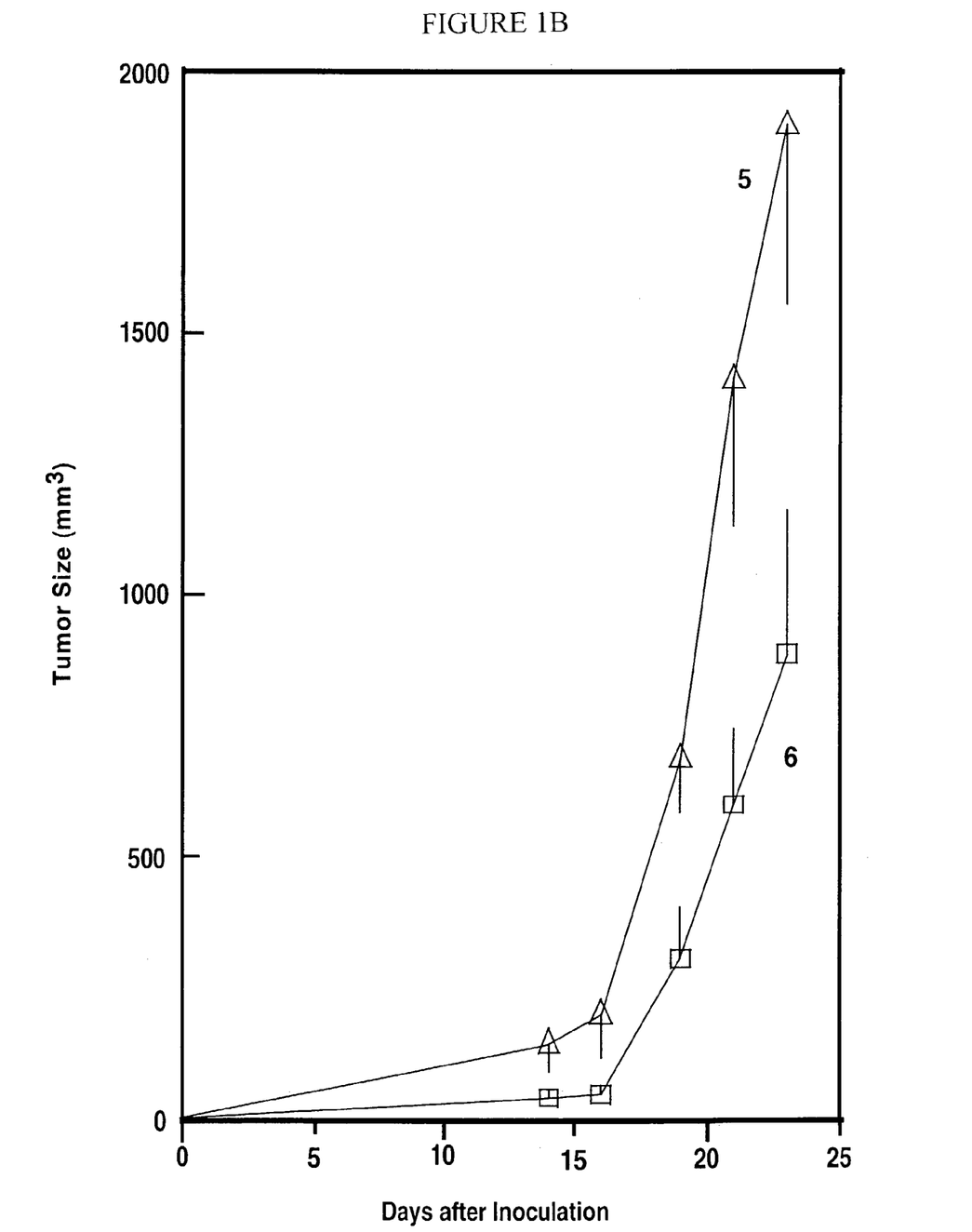

Mouse Lung Tumor Model: In Experiment I, tumor size was measured on the 10th, 12th, 14th, 17th, and 22nd day after the inoculation of tumor cells (FIG. 1A). Curves #1, #2, #3, and #4 in FIG. 1A depict the mean tumor size in mice consuming Food #1, #2, #3, and #4 respectively measured after inoculation. Each point is mean+SE. The percent inhibition of tumor growth rate in groups #2, #3, and #4 compared with the control (#1) were 16%, 49%, and 82% on the 14th day and 53%, 60%, and 82% on the 22nd day respectively. Both mung bean (#2) and mushroom extract (#3) showed clear inhibition of tumor growth and these effects were additive when both extracts (#4) were used in combination. In Experiment II, tumor size was measured on the 14th 16th, 19th, 21st, and 23rd day after tumor inoculation (FIG. 1B). Curves #5 and #6 in FIG. 1B are the mean tumor size in mice using Food #5 and #6. Each point is mean+SE. Lab Chow containing 5% DSV produced 53-74% inhibition in tumor growth rate in the first 23rd days. One of 8 mice showed partial tumor regression after 26th day and complete regression after 32 days. The weekly food consumption per mouse of preparations #1 to #6 was 16.9+1.4 g, 18.9+0.8 g, and 16.0+0.6 g in the first, second, and third week after tumor inoculation. No appreciable difference between groups was found.

Patient Characteristics: The patients' gender, age, stage, cell type, metastatic sites, conventional treatments to the primary tumor and metastatic lesions respectively, tumor response, complications, and KPS are summarized in Table 2. Occurrence of metastatic disease after ingesting SV, the length of time taking SV, the duration of tumor-free status, and survival are also summarized in Table 2.

TABLE 2

Patients Characteristics and Survival Time with Adjuvant SV to Therapy

| Tumor Case/Sex/Age | Stage T.N.M. | Cell Type | Metastatic Site | Primary Tumor | Metastatic Tumors | Tumor Response[1] | Other Complications | New T after SV | KPS[2] (a) | KPS[2] (b) | using SV | Time (Months)[3] Free | Survival |
|---|---|---|---|---|---|---|---|---|---|---|---|---|---|
| A. Lead Cases: | | | | | | | | | | | | | |
| 1 F 69 | IV: 2.2.1. | lrg | adrenal | S | C, R, SV, smancs, S | no residual T | no | no | 40 | 100 | 27 | >133 | >137 alive |
| 2 F 75 | IV: 2.1.1 | adn | brain | S | SV, R, smancs | complete | malnutrition[P2] | no | 40 | 80 | 12 | 10 | 14 |
| B. Study Group | | | | | | | | | | | | | |
| *a. Complete Response of Metastatic Tumors and No Recurrent Tumor After Using SV Alone* | | | | | | | | | | | | | |
| 3 F 57 | IV: 1.3.1. | adn | both lungs | S | SV | complete | no | no | 50 | 100 | >35 | >30 | >39 alive |
| 4 F 73 | IV: 1.3.1. | adn | both lungs | S | SV | complete | no | no | 90 | 100 | >27 | >12 | >28 alive |
| *b. Complete Response, Partial Response, or Stabilization of Metastatic Tumor after Using SV and Other Treatments* | | | | | | | | | | | | | |
| 5 F 80 | IV: 4.2.1. | adn | vert, pleu ef | R | R, SV | stable/prog | no | no | 50 | 90 | >46 | 0 | >48 alive |
| 6 M 67 | IIIB: 4.2.0. | adn | pleural eff | no | PD, SV, R, C | partial | nerve injury[P6] | yes | 50 | 90 | 43 | 0 | 45 |
| 7 F 34 | IIIB: 2.3.0. | nsc | contral l.n. | S | C, SV, R, | no residual T | no | no | 50 | 100 | >32 | >30 | >33 alive |
| 8 F 78 | IIIB: 4.0.0. | adn | pleural eff | S | R, C, SV | stable | pneumonia | no | 50 | 100 | >21 | >20 | >28 alive |
| 9 M 69 | IV: 2.0.1. | adn | brain, bone | S | R, SV | complete | no | yes | 50 | 100 | 16 | na | 22 |
| 10 F 51 | IV: 1.2.1. | adn | brain | S, C, R | SV, R, S | no residual T | depression[P10] | yes | 50 | 90 | 14 | na | 20 |
| 11 F 59 | IV: 1.1.1. | adn | brain | no | SV, R | stable/prog | v. thromboses[P11] | no | 50 | 90 | 10 | 0 | 11 |
| 12 M 58 | IV: 2.3.1. | adn | adrenal | S, C | C, SV, C | stable/prog | heart[P12] | no | 60 | 70 | 9 | 0 | 12 |
| 13 F 76 | IIIB: 4.3.0. | adn | pleural eff | S | C, R, SV | complete | no | no | 50 | 100 | 5 | 2 | >8 alive |
| 14 F 47 | IIIB: 4.3.0. | adn | pleural eff | C | C, SV | | na | na | 50 | 50 | 5 | 0 | 6 |
| Average Karnofsky Performance Status (Pts #3–#14) | | | | | | | | | 54 ± 12 | 90 ± 15 | | | |
| C. Ineligible Patients[4] | | | | | | | | | | | | | |
| 15 M 40 | IIIA: 1.2.0. | adn | | C, R | SV | | nausea, vomiting | | | | 1.5 | 0 | 10 |
| 16 M 56 | IV: 4.0.1. | sqm | vert | R | R, SV | | paraplegia | | | | 1.4 | 0 | 5 |
| 17 M 64 | IV: 4.0.1. | adn | brain, bone | S, C | SV | | | | | | 0.2 | 0 | 6 |
| 18 M 57 | IV: 4.0.1. | adn | spine, rib | C, R | SV | | | | | | 0.5 | 0 | 3 |

Tumor Response[1]: No Tumor: Patient had no detectable tumor subsequent to surgical resection. Complete: Complete regression. Stable: Tumor stopped growing. Stable/prog: Tumor was stable first and then progressed. Partial: Partial regression.
KPS[2]: Karnofsky Performance Scale; (a) KPS at the time of starting SV. (b) KPS after using SV for 5 months or more.
Time (Months)[3]: Months ingesting SV, remaining tumor free, or surviving at last observation.
Ineligible Patients[4]: Pt #15, 17, 18 ingested SV at less than full dosage and Pt #15–18 for less than 2 months. These patients did not meet the entry criteria and were excluded from the evaluation of MST.
Abbreviations:
Lrg: Large cell carcinoma.
nsc: non-small cell carcinoma;
adn.: adenocarcinoma;
sqm.: squamous cell carcinoma.
S.: surgery;
C: chemotherapy;
R: radiotherapy;
PD: pleurodesis;
pleural eff: pleural effusion;
vert: vertebrae;
v: vein.
l.n.: lymph node(s);
na: data not available.
[P2]Patient had anorexia and severe malnutrition during smancs therapy and died from aspiration pneumonia.
[P6]Patient suffered severe pain due to pleurodesis-related thoracic nerve injury. He was treated with Elavil, ibuprofen, atenolol, Fentanyl, Decadron, and bupivacaine.
[P10]Patient was treated with Decadron, Klonopin, methadone, Elavil, and Duragesic.
[P11]Patient suffered extensive deep vein thromboses and was treated with Decadron and phenobarbital after her tumor was stabilized.
[P12]Patient had coronary artery bypass surgery.

Lead Cases:

Case #1: A stage IV patient whose tumor progressed while on chemotherapy and radiotherapy has been tumor-free for 133 months after ingestion of SV, SMANCS therapy, and resection of a metastatic lesion.

Patient #1 had a poorly differentiated large cell carcinoma in her RLL (2.2×2 cm) with a positive subcarinal lymph node (Table 2). A lobectomy in 1/85 was followed with methotrexate, adriamycin, CCNU, and cytoxan. Her disease progressed with metastasis to left adrenal gland (4×3 cm, 8/85), a right pleural effusion developed, and her KPS dropped to 40. Her adrenal tumor did not respond to radiotherapy and continued growing (5×4 cm, 11/85). She began ingesting SV daily from 9/85. She was also treated with SMANCS, which is the antitumor protein, neocarcinostatin, conjugated with a polystyrene-maleic acid copolymer (35), and had adrenalectomy in 12/85. The adrenal tumor was well encapsulated containing mostly necrotic tissue. She continued SMANCS for 4 months and ingested SV daily until 12/87. She remains tumor-free.

Case #2: Complete regression of three metastatic brain tumors

Patient #2 had a well differentiated adenocarcinoma in RUL (Table 2). She had a lobectomy in 3/86. In 10/86, CT scan showed 3 metastatic brain lesions (FIG. 2). KPS was 40. She started SV, SMANCS, and a one month course of radiotherapy. All 3 tumors disappeared completely in 4 months. She continued SV and SMANCS therapy until 6/87. During this time she developed anorexia and severe malnutrition, followed by aspiration pneumonia and sepsis, and died in 12/87 without clinical signs of tumor recurrence.

Figure 3:
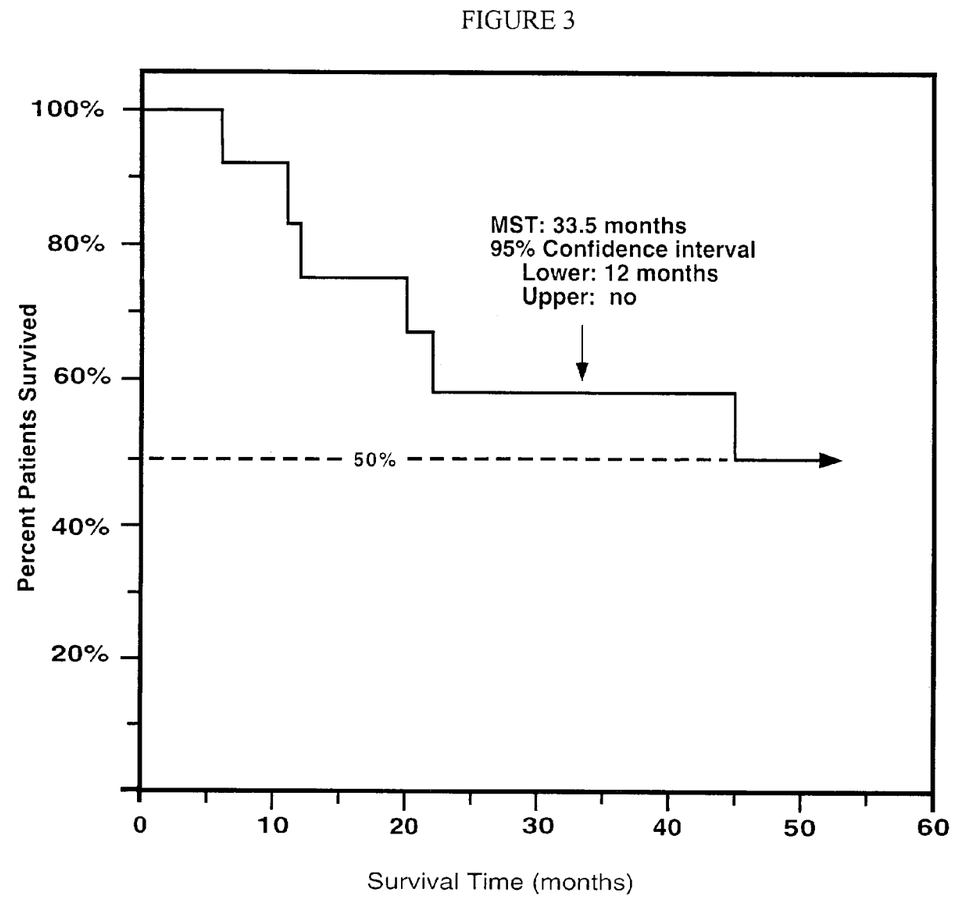
FIG. 3 shows the median survival time of Stage III B and IV non-small cell lung cancer patients in the pilot study.

Median Survival Time: Five stage IIIB and 7 stage 1V patients were eligible for analysis (Patients #3-14). Half of these patients were still alive at the closing date; thus, the MST was not reached according to Kaplan and Meier (Kaplan EL, Meier P. Nonparametric estimation from incomplete observations. J Am Stat Assoc 1958; 53: 457-82). A conservative estimate of 33.5 months, namely, the midpoint of the survival curve above the median, i.e., between 22 and 45 months, was chosen as the MST (FIG. 3). As shown in FIG. 3, the survival of 12 patients (#3 to #14, Table 2) was plotted and analyzed according to Kaplan and Meier. The MST should be 45 months and the 95% confidence interval had a lower boundary of 12 months and no upper boundary reached. For conservative evaluation, the midpoint of the survival curve above the median was chosen as MST, namely, between 22 and 45 months or 33.5 months. The 95% confidence interval had a lower-boundary of 12 months and no upper-boundary. One-year survival was 75%.

New Tumors: Ten of the 14 patients (#1-5, 7, 8, 11-13, Table 2) had no new sites of metastasis after conventional treatments and SV therapy. Patient #14 suffered severe side-effects of concurrent chemotherapy and was not evaluated for new tumors.

SV Therapy Alone: Both patient #3 and #4 had complete regression of their multiple metastatic lesions in both lungs after using SV alone for 5 and 15 months and remained tumor-free, 39 and 28 months after diagnosis. After unsuccessful radiotherapy and while using SV alone, the pulmonary and vertebral body lesions of patient #5 were stable for 40 months and subsequently progressed slowly. She was still alive at the conclusion of this study.

Figure 4A:
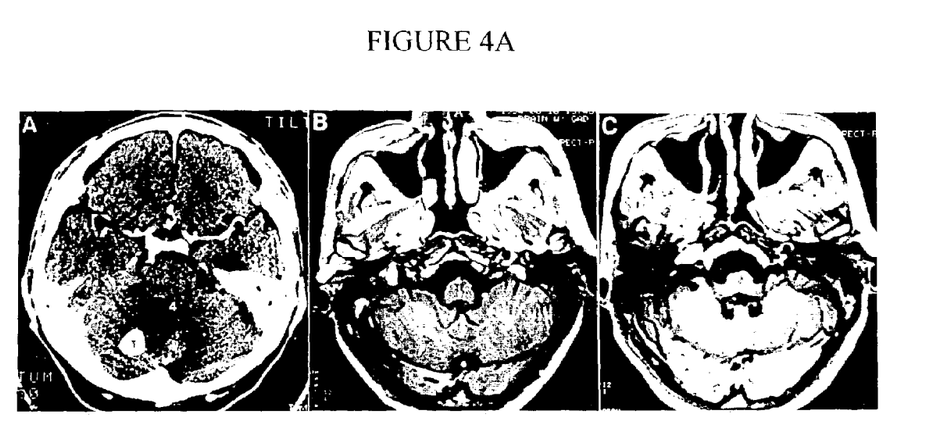
FIG. 4a shows the right cerebellar metastasis of patient #9 in the pilot study.
Figure 4B:
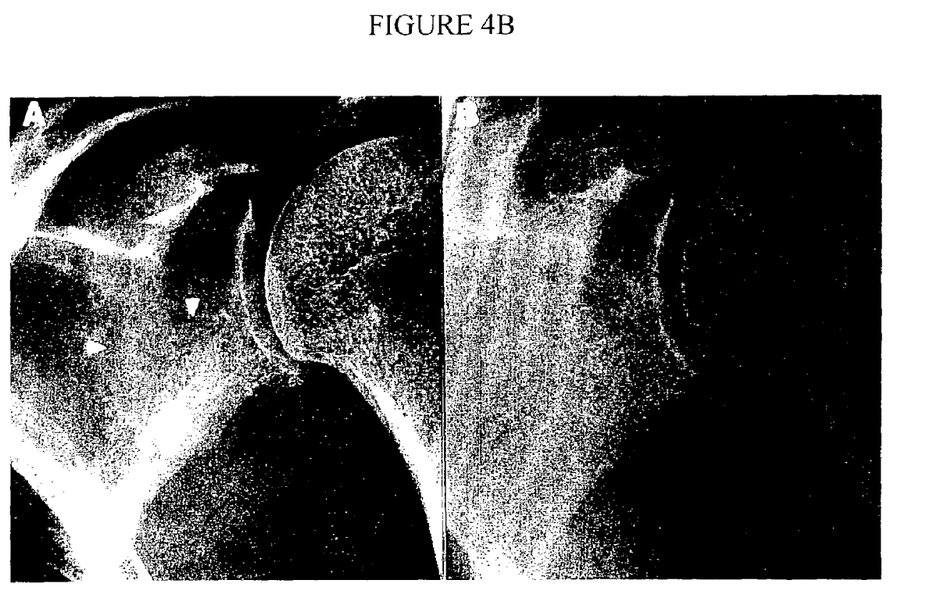
FIG. 4b is a radiograph of a left scapula of patient #8 in the pilot study.

SV and Radiotherapy: Of the four patients who had brain metastases, three (#2, #9, 10) achieved complete regression after using SV and radiotherapy. Both lesions in brain and bone of Patient #9 regressed completely after radiotherapy. FIG. 4 is a right cerebellar metastasis of patient 9. FIG. 4A shows in A is a post contrast CT scan in superior orbitomeatal plane taken on Dec. 17, 1992. An enhancing metastatic lesion (T) of 1.5×1.2× approximately 1.2 cm in size, located in the quadrangular lobule of the cerebellum on the right side with considerable edema (low density area) of the surrounding area, particularly anteriomedially. The fourth ventricle (4) was displaced anteriorly and to the left. The vermis (V) was also displaced to the opposite side. The posterior fossa cisterns were narrow on the right (unlabelled double arrow). FIG. 4A also shows B and C, which shows a post gadolinium MR section in exaggerated inferior orbitomeatal plane taken on Jun. 16, 1994. Because of considerable difference in sectional angles between A and B & C, two consecutive MR sections (B &C) were selected in order to amply cover the original site of the cerebellar metastasis. The enhancing tumor attenuated and was no longer detectable in post gadolinium axial MR T1 weighted image. Unlabelled single arrow in two consecutive MR images indicates the presumptive location of the original cerebellar metastatic lesion seen in A. The fourth ventricle (4) and the vermis (V) have returned to their normal positions. The edema surrounding the tumor seen before the treatment was not observed. FIG. 4B is a radiograph of the left scapula of patient #8. In A, the radiograph of left scapula shows a mixed osteoblastic and osteolytic lesion (white arrowhead) in the inferior aspect of the glenoid process, due to metastatic cancer. In B, the radiograph of left scapula 12.5 months later shows that the lesion in the glenoid process has much improved. Patient #11 had radiotherapy to her left cerebellar brain lesions; her primary tumor and the multiple lesions in her brainstem remained stable without radiotherapy for 10 months.

Toxicity and Performance Status: Patients ingested SV daily for 5 to 46 months. Except for patient #14 whose condition was adversely affected by concurrent chemotherapy, all patients in the cohort (#3-#13) showed no toxic complications attributable to SV. Their blood chemistry values revealed no compromise in hematological, renal, hepatic, and metabolic function; they all showed a significant improvement in KPS after ingesting SV for 5 months (Table 2). Average KPS values increased from 54+12 to 90+15 ($p<0.01$).

Discussion

The benefits of fruits and vegetables for cancer prevention has been emphasized by both NCI and ACS and are considered as major causes of the reduction in cancer rates and related deaths. The present report describes the pursuit of an unexpected clinical observation and provides data suggesting that a mixture of edible plants, specifically selected for their antitumor attributes, may benefit patients who already have advanced cancer.

The MST of stage IIIB and IV NSCLC has changed little in recent decades. Therefore, historical controls can be used to provide comparison for the results observed here. In a review of 8 randomized trials of chemotherapy versus supportive care for stage III-IV NSCLC, the MST's of the untreated groups were 5 months or less and 7-8.5 months in the chemotherapy groups (4). The MST for the 12 patients who used SV for 2 months or longer was 33.5 months. The sample size was small, but all patients had advanced disease; moreover, objective responses to SV were observed in this cohort and in one tumor-bearing mouse.

NSCLC patients with CNS metastases have a MST of 3-4 months with radiotherapy and complete regression is rare (39-41). Of 4 patients with CNS involvement, three (#2, 9, 10) had complete remission of CNS lesions and the fourth (#11) had a partial response after radiotherapy and SV use. The complete regression of metastatic tumors in both brain and bone (#9), and multiple brain lesions (#2) is unexpected. Recurrence of malignant pleural effusions and new metastases are common in stage III-IV patients. Ten of 14 patients developed no new metastatic sites during this study period.

Patient selection bias is a major consideration in clinical trials. It is essential to consider sources of potential bias especially when clinical outcomes differ markedly from historical controls. Four patients (#15-18) who ingested SV for less than 2 months were not included in the survival analysis; their survival times (3 to 10 months) were within the expected historical range. Other possible bias could result from the self selection of highly motivated patients who sought new treatments after failing to benefit from conventional therapies and who were willing to make a commitment to daily SV use often with strong family support. Cassileth et al. report a weak link between cancer survival and social ties, but these authors concluded that clinical factors (e.g. stage, KPS, weight loss) but not psychosocial factors (e.g. "hopefulness") could be considered predictors of survival. Whereas patient compliance may be related to treatment efficacy, psychological factors alone are unlikely to result in a three-fold increase in MST or in complete tumor regression in patients using SV alone. The inhibition of tumor growth observed in the mouse model further supports the hypothesis that some combination of ingredients in SV may have direct anti-tumor or immune modulating activity.

Large clinical trials of advanced NSCLC often have a small number of patients with long survivals. It could be argued that by chance or selection bias such patients were overrepresented in this cohort. This is unlikely because of many instances of poor prognostic status and failed treatment history in this cohort when SV was initiated. Furthermore, complete and partial tumor regression and improved KPS after using SV alone are objective responses to SV, which are not affected by patient differences or by patient number. The potential causes of long survivorship have received relatively little attention, although such studies may yield clues for improved cancer treatment. Among these possible causes, diet supplements are widely accessible and some are supported by scientific studies. This approach, which uses a specific dietary supplement, was ingested by the 2 lead patients and this cohort.

Well-known prognostic indicators for survival in NSCLC include stage of disease, KPS, and weight loss. KPS values increased from an average of 54+12 to 90+15 in 5 months after SV use. In a prior study, the KPS of stage III and IV NSCLC patients of SV-treated group also improved but it decreased in the untreated control group; similarly the MST also improved significantly (3-fold). Body weight data were not available in the current study. In the prior study, however, the weight change was −2.1+2.3% in the SV-treated group but −11.6+4.9% in the control group. In both studies, blood chemistries revealed no evidence of toxicity in patients ingesting SV daily for 5-46 months. Significantly improved performance status and absence of toxicity are concordant with the prolonged survival times of these patients.

The immunostimulatory and antitumor effects of purified beta-glucans (e.g., lentinan, pachymaran, zymosan, schizophyllan) and peptidomannan (KS-2) have been well documented. Other studies have identified antitumor actions of soybean components, e.g., protease inhibitors, inositol hexaphosphate, coumestrol, daidzein, biochanin A, and genistein. Four of these components were quantitatively identified in SV; others are reported to be present in the vegetables contained in SV. The most abundant ingredients in SV are soybean, mushroom, and mung bean. Because Purina Lab Chow already contains soy protein, the antitumor activities of mushroom and mung bean were tested individually and in combination. Combining mushroom and mung bean extracts produced the greatest inhibition of tumor growth (82%) in the mouse model indicating that certain combinations of foods may be more carcinostatic.

The multiple instances of tumor response coupled with increased survival times, attenuation of disease progression, and consistent improvement in performance status indicate that SV therapy, as an adjuvant to surgery and radiotherapy, should be evaluated further in a large, randomized study of NSCLC patients.

EXAMPLE 2

Phase I/II Study of Stage III and IV Non-Small Cell Lung Patients Selection of Patients All the stage III and IV NSCLC patients who first attended the Lung Clinic, School of Medicine, University of Palacky, from June 1992 to January 1994 and met the entry criteria were invited to participate in the study. All eligible patients who did not use SV served as the control group (13 patients). Cooperative group phase II-III investigation entry criteria were used: $\leq 70$ years of age; ability to eat well; adequate gastrointestinal, hepatic, renal, and cardiopulmonary function; and Karnofsky performance status (KPS) $\geq 70$. Exclusion criteria were white blood cells <4,000/ml, platelets <100,000/ml, bilirubin >1.5 mg/dl, creatinine >1.5 mg/dl, blood sugar >200 mg/dl, prior malignancy, myocardial infarction, uncontrolled hypertension, arrhythmia, serious infection, psychiatric disorder, unreliability, or noncompliance. In addition to the entry criteria, prognostic factors for survival, including stage, previous and concurrent therapies, tumor cell type, age, gender, KPS, and body mass index (BMI) were compared in all groups. Twelve patients agreed to ingest SV: six at stage III and IV in the treatment group (SVG) and five at stage I in the toxicity study group (TG); one patient was first diagnosed as having adenocarcinoma but was excluded from analyses because she was later identified as having colon cancer in 1983. All patients were offered standard conventional therapies. Patients were followed until death or 24 months from the date of entry.

Study Period, Survival Time, and Statistical Analyses

This study was designed to test the null hypothesis ($H_0$) that the median survival times of the stage III and IV patients in the treatment group (SVG) and the control group (CG) will be the same. The alternative hypothesis ($H_2$) is that the MSTs of the two groups will be different. The study period was 24 months from the starting date (date of diagnosis). The survival time was calculated from the starting date to the date of death or to the cutoff date. The Kaplan-Meier method and log-rank test were used to calculate and compare the median survival times and the 95% confidence intervals. The Wilcoxon Rank and Sum test was used to compare mean survival times between the two groups. Student's t-test was used to compare the ages, KPS, and percent weight change.

Diagnosis, Staging, and Survival Time

NSCLC was diagnosed by histopathology and/or cytopathology and reviewed by a pathologist. The size and location of the tumors were determined with radiographs by the treating physicians and a radiologist and reviewed by another radiologist. Staging was assigned according to the American Joint Committee on Lung Cancer. The most conservative interpretation was used for analyses.

Treatment

All patients were treated with conventional therapies, including radiation, surgery, and/or chemotherapy, selected by the treating physicians independently of the use of SV. SV was included as part of the daily diet of the treatment group patients. The intended duration of treatment with SV was 24 months; participating patients were encouraged to ingest SV soon after diagnosis and for the entire period. All eligible patients who ingested SV were included in the analyses.

Thirty grams of freeze-dried SV powder were mixed with one cup of water or other soup and ingested daily. Patients were interviewed and examined monthly, except for four patients (Patients 5, 6, 8, and 10, Table 2) who were unable to keep their clinical appointments. Computed tomography scans were performed at entry and then every six months or sooner if clinically needed. Body weight and KPS were evaluated at the study entry and one to three months thereafter. Chest films, spirometry, and blood chemistry were performed at entry and when clinically required or bimonthly.

Nutrition Data

Random samples of SV were sent to Northeast Laboratories for determination of their nutritional values. A 30-g daily serving of SV (dry weight), on the basis of percentage of daily requirement of a 2,000-calorie diet contains 11 g (4%) carbohydrate, 11 g (24%) protein, <1 mg fate, 8 g (36%) dietary fiber, <1 mg cholesterol, 102-110 cal gross food energy, and 84-90 cal physiological fuel value.

Toxicity

The toxicity of SV was evaluated in all patients who had ingested SV. To minimize the confounding effects of advanced disease and therapeutic toxicity, five stage I NSCLC patients were invited to take SV daily. Their clinical status was evaluated monthly, and blood chemistries were obtained at entry and bimonthly. Clinical signs of toxicity, such as fatigue, vomiting, nausea, diarrhea, fever, headache, hair loss, mucosal ulcerations, and skin rashes were evaluated. In addition, changes in appetite and in the frequency of sexual activity and exercise before and after diagnosis of NSCLC and before and after taking SV daily were also evaluated.

Informed Consent

The protocol for the clinical trial was approved by the Committee for Research on Human Subjects at the University of Palacky School of Medicine. Informed consent was obtained from all patients in the treatment and toxicity study groups.

Results

Patient Characteristics

The control group (CG) consisted of five patients at stage IV, four at stage IIIB, and four at stage IIIA (Table 2). The age of the patients was 40-65 years, with an average of 54.3±8.8 years. At entry their body mass index (BMI) was 19.5-36.5, with an average of 26.7±5.5, and their KPS was 70-90, with an average of 78.5±8.0. Thirty-one percent of the CG patients were women. In the treatment group (SVG), 6 patients were eligible: one was a woman, two were at stage IV, three at stage IIIB, and one at stage IIIA (Table 3). Their age was 41-55 years, with an average of 49.2±4.7 years. At entry their BMI was 24-30.7, with an average of 27.0±2.7, and their Karnofsky performance scale (KPS) was 70-90, with an average of 75±8.4. Student's t-test was used to compare the age, BMI, and KPS at entry of the SVG patients with those of the CG patients, yielding $p>0.1$.

Five stage I patients were in the toxicity study group (TG) (Table 3). At study entry their age was 41-68 years, with an average of 54.6±11.3 years; their BMI was 22.2-27.7, with an average of 24.7±2.4; and their KPS was 70-90, with an average of 78.0±8.4. One other patient (Patient 12, Table 3) had colon cancer in 1983 and was presumed to have metastatic colon cancer on review and was excluded from the analyses.

Weight Change

At entry BMIs of CG, SVG, and TG patients were 26.7±5.5, 27±2.7, and 24.7±2.4, respectively ($p>0.1$, Student's t-test). None of the patients was severely underweight, and all BMIs were >19. The body weight of nine CG patients was measured one to three months after entry (except for Patient 1), and all lost 3.7-17.7% of their body weight, with an average loss of 11.6±4.9% (Table 2). In the SVG patients who did not receive chemotherapy, there was no change or a loss of <1.5% of body weight within the first seven month after entry; those with concurrent chemotherapy lost 4.8% and 5.2% (Table 3). Similarly, the two CG patients (Patients 9 and 13, Table 2) who were treated with chemotherapy lost more weight (17.7% and 16.4%, respectively) than the average (11.6%). The average weight loss of the SVG patients within the first seven months after entry was 2.1±2.3%. When the change in body weight between the two groups was compared, $p<0.01$.

The TG patients either gained or had no change in their weight measured 4-12 months after entry, with an average weight gain of 4.0±3.9%. The ineligible patient (Patient 12) showed no weight change.

Performance Status

Within the first three months after entry, virtually all the CG patients deteriorated rapidly, i.e., their KPS declined to 40-70, with an average of 55.4±11.3 ($p<0.01$ compared with KPS at entry) (Table 3). Except for one patient, the condition of the SVG patients improved or remained the same, and their KPS was 60-90, with an average of 80±13 ($p>0.1$ compared with KPS at entry) (Table 4). The KPS of the CG and SVG patients after entry were compared, yielding $p<0.01$.

Four of the SVG patients not receiving chemotherapy showed an increase or no change in KPS. In the two patients treated with concurrent chemotherapy, there was a decrease or no change in KPS (Table 4). The condition of all TG patients and of the ineligible patient (Patient 12) improved, and all were alive and well at 24 months, with KPS of 90.

TABLE 3

Patient Characteristics: No Ingestion of SVs[a]

| Patient No. | Age | Gender | Cell Type | Stage: TNM[b] | Treatments | KPS At entry | KPS After treatment[c] | BMI, kg/m$^2$ | % Wt Change[d] | Survival, mo |
|---|---|---|---|---|---|---|---|---|---|---|
| 1 | 65 | M | Squamous | IV: 3.2.1. | R | 80 | 60 (3) | 27.1 | −11.0 (7) | 8 |
| 2 | 59 | F | Adenocarcinoma | IV: 2.2.1. | R | 80 | 50 (3) | 36.5 | −3.7 (1) | 5 |
| 3 | 54 | M | Squamous | IV: 2.2.1. | R | 70 | 50 (3) | 23.6 | −13.2 (2) | 4 |
| 4 | 45 | M | Squamous | IV: 1.3.1. | R | 80 | 50 (2) | 28.0 | −7.7 (3) | 3 |
| 5 | 46 | F | Undifferentiated | IV: 2.1.1. | S, R | 70 | 40 (2) | 22.9 | NA | 3 |
| 6 | 50 | M | Squamous | IIIB: 4.2.0. | R | 80 | 70 (1) | 26.1 | NA | 1 |
| 7 | 56 | F | Poorly differentiated | IIIB: 3.3.0. | R | 80 | 60 (3) | 31.2 | −8.2 (1) | 7 |
| 8 | 60 | M | Squamous | IIIB: 4.0.0. | S, R | 70 | 40 (3) | 26.6 | NA | 4 |
| 9 | 62 | M | Adenocarcinoma | IIIB: 4.1.0. | C | 90 | 40 (2) | 27.5 | −17.4 (2) | 4 |
| 10 | 65 | M | Squamous | IIIA: 3.2.0. | SC | 90 | 70 (1) | 21.1 | NA | 2 |
| 11 | 62 | M | Squamous | IIIA: 3.1.0. | R | 70 | 60 (3) | 22.5 | −17.7 (3) | 12 |
| 12 | 42 | M | Adenocarcinoma | IIIA: 2.2.0. | R | 70 | 60 (1) | 36.3 | −8.7 (1) | 2 |
| 13 | 40 | F | Adenocarcinoma | IIIA: 3.2.0. | C, R | 90 | 70 (3) | 19.5 | −16.4 (3) | 7 |
| Mean ± SE | 54.3 ± 8.8 | | | | | 78.5 ± 8.0 | 55.4 ± 11.3 | 26.7 ± 5.5 | −11.6 ± 4.9 | 4.8 ± 3.0 |

[a]Abbreviations are as follows: SVs, selected vegetables; M, male; F, female; R, radiotherapy; C, chemotherapy; S, surgery; SC, supportive care without R, S, or C; NA, not available; KPS, Karnofsky performance scale; BMI, body mass index.
[b]International staging system for lung cancer.
[c]Months after treatment in parentheses.
[d]Percentage of weight lost between first and later visit, with months between measurements in parentheses; weight measured at first visit was used as denominator.

TABLE 4

Characteristics of Patient Who Ingested SV[a]

| Patient No. | Age | Gender | Cell Type | Stage and TNM[b] | Treatments | KPS At entry | KPS After treatment[c] | BMI, kg/m$^2$ | % Wt Change[d] | SV mo | Survival, mo |
|---|---|---|---|---|---|---|---|---|---|---|---|
| | | | | Stage III and IV patients for survival study | | | | | | | |
| 1 | 50 | M | Squamous | IV: 2.2.1. | R | 70 | 90 (3) | 26.1 | −1.2 (5) | 7 | >24 |
| 2 | 49 | M | Squamous | IV: 2.1.1. | R | 70 | 80 (3) | 30.7 | 0.0 (5) | 5 | 16 |
| 3 | 52 | M | Adeno-carcinoma | IIIB: 4.1.0. | R | 80 | 90 (3) | 24.0 | −1.3 (7) | 17 | 18 |
| 4 | 55 | M | Squamous | IIIB: 2.3.0. | C | 70 | 70 (3) | 29.4 | −4.8 (6) | 4 | 9 |
| 5 | 41 | F | Adeno-carcinoma | IIIB: 4.3.0. | C | 70 | 60 (3) | 27.3 | −5.2 (3) | 7 | 8 |
| 6 | 48 | M | Adeno-carcinoma | IIIA: 2.2.0. | R | 90 | 90 (3) | 24.1 | 0.0 (3) | 4 | 15 |
| Mean ± SE | 49.2 ± 4.7 | | | | | 75 ± 8.4 | 80 ± 13 | 27.0 ± 2.7 | −2.1 ± 2.3 | | |
| | | | | Stage I patients for toxicity study | | | | | | | |
| 7[e] | 41 | M | Squamous | I: 2.0.0. | S, R | 70 | 90 (3) | 24.1 | 2.3 (12) | >24 | >24 |
| 8 | 63 | M | Squamous | I: 1.0.0. | R | 90 | 90 (3) | 26.7 | 0.0 (5) | >17 | >24 |
| 9 | 68 | M | Squamous | I: 1.0.0. | R | 80 | 90 (3) | 27.7 | 7.5 (7) | >20 | >24 |
| 10 | 55 | M | Large cell | I: 2.0.0. | R | 70 | 90 (3) | 22.2 | 8.8 (8) | >20 | >24 |
| 11 | 46 | M | Squamous | I: 2.0.0. | R | 80 | 90 (3) | 22.6 | 1.3 (4) | >18 | >24 |
| Mean ± SE | 54.6 ± 11.3 | | | | | 78.0 ± 8.4 | 90.0 ± 0.0 | 24.7 ± 2.4 | 4.0 ± 3.9 | | |
| | | | | Ineligible patient | | | | | | | |
| 12[f] | 47 | F | Adeno-carcinoma | N/A | S, C, R | 70 | 90 (3) | 31.2 | 1.2 | >24 | >24 |

[a]See Table 2 footnote for definition of abbreviations.
[b]International staging system for lung cancer.
[c]Months after treatment in parentheses.
[d]Percentage of weight lost between first and later visit, with months between measurements in parentheses; weight measured at first visit was used as denominator.
[e]Patient 7 had lesions in both adrenal glands, but no biopsy was performed.
[f]Patient 12 had colon cancer in 1983 and was excluded from analyses. Her lung tumor was presumed to be metastatic colon cancer.
N/A, not applicable.

Survival Time

Figure 5:
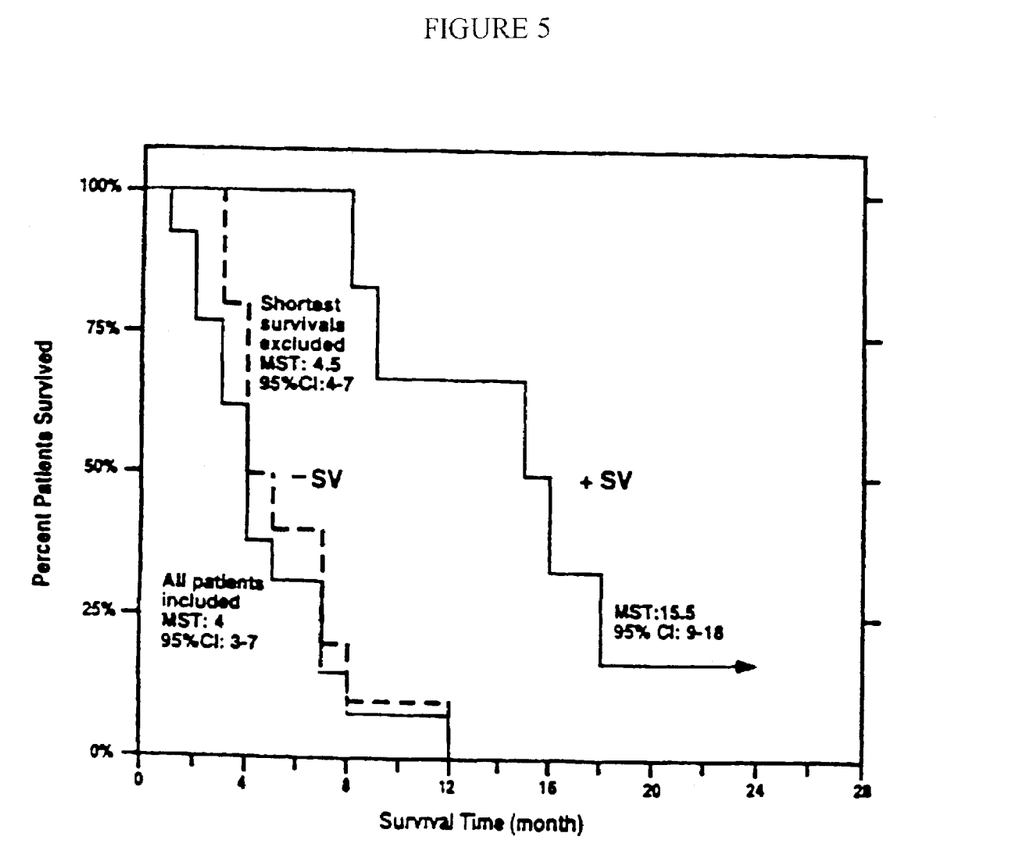
FIG. 5 illustrates the survival times of stage III and IV non-small cell lung cancer patients with and without the selected vegetable treatment.

The CG patients survived from 1 to 12 months, and all died before the cutoff date, with an average survival time of 4.8±3.0 months (Table 3). The median survival time was four months with a 95% confidence interval of three to seven months (FIG. 5). If the worst survivors (Patients 6, 10 and 12) were excluded from evaluation, the remaining patients survived for 3-12 months, and the median survival time was 4.5 months, with a 95% confidence interval of 4-7 months, with an average survival time of 5.7±3.0 months.

SVG patients ingested SV for 4-17 months. The median survival time was 15.5 months, and its 95% confidence interval was 9-18 months, and one patient survived >24 months (FIG. 5). In the log-rank test comparing median survival times of the SVG and the CG patients (including or excluding Patients 6, 10, and 12), p<0.01, indicating that the median survival time of the SVG patients is significantly longer than that of the CG patients. Thus, $H_0$ is not supported by the data and rejected, but $H_2$ is supported and accepted. If Patient 1 was assumed to be dead at the cutoff date (Table 4), the Wilcoxon Rank and Sum test for small sample size could then be used. The mean survival times of the SVG and the CG patients were 15 and 4.8 months (or 5.7 months excluding the worst survivors), respectively, with p<0.01, indicating that the former is significantly longer than the latter. Again $H_0$ is not supported by the data and rejected, but $H_2$ is supported and accepted.

One patient (Patient 7) had lesions in both adrenal glands, but no biopsy was performed. He was classified as stage I for toxicity evaluation only. One other patient (Patient 12) had colon cancer in 1983 and was presumed to have metastatic colon cancer on review. Both patients were alive and well beyond 24 months, but they were not included in survival analyses.

Toxicity Evaluation of Patients Ingesting SV

All patients who ingested SV (Table 4) showed no clinical signs of toxicity (see Materials and Methods). Their blood chemistry data indicated that no significant hematologic, renal, or hepatic toxicity occurred. The five stage I TG patients ingested SV daily for 17-24 months (Table 4). All were treated with radiotherapy and/or surgery, but not chemotherapy. None of these patients showed weight loss, bleeding, or any clinical symptoms of gastrointestinal, neurological, or cardiopulmonary dysfunction. All were alive and well with stable tumor at the end of the 24-month study period. They maintained or resumed routine activities, including daily full-time work, exercise, and sexual activity. No clinical signs of toxicity were detected. None developed new tumor during the study period. Some patients reported a feeling of fullness or bloatedness after ingesting SV, and some found it difficult to consume 30 g of SV daily. A few patients did not care for the taste of SV. Nonetheless, all five TG patients ingested SV daily for >17 months.

Discussion

This exploratory study tests the hypothesis that the daily ingestion of a combination of foods that contain different types of antitumor components may benefit patients with stage III and IV NSCLC. Several vegetables contain molecularly defined components with immune-modulating or antitumor activity (Table 1). The individual activities, although well documented, have only modest potencies. They have different mechanisms of action and thus may act synergistically when used together. These antitumor entities are not toxic. Adding them to the daily diet of cancer patients incurs minimal risk.

Conventional therapies afford only marginal benefit for stage IIIB and IV NSCLC. The median survival time of stage IIIB and IV NSCLC patients is usually short. Thus, adding a dietary supplement to the patients' daily diet without interfering with conventional therapies was deemed ethical, and adequate clinical observation could be achieved within 24 months.

The number of SVG patients is small, but the difference in median survival times between CG and SVG patients is large (3-fold). The Log-Rank test showed p<0.01 and no overlap in the 95% confidence intervals of the two median survival times, indicating a significant difference between SVG and CG patients. Furthermore, using the Wilcoxon Rank Sum test, which could also be used to compare groups of small sample size, the mean survival time of the SVG patients is also statistically longer than that of CG patients (p<0.01). Moreover, using even more conservative evaluation, if the CG patients with the shortest survivals (Patients 6, 10, and 12) are excluded from analysis, the median survival time and mean survival time of CG patients are still significantly different from those of SVG patients (p<0.01).

Most patients failed to ingest SV for the intended period, but all patients ingested SV for four months or longer. Failure to ingest SV for the intended period was mostly due to lack of motivation and confidence in the efficacy of SV, boredom and monotony in taking 30 g of SV powder daily, taste preference of patients unaccustomed to high-fiber, low-fat foods, bloating, fullness, and cancer-related anorexia. SVG patients (stage III-IV), except for Patient 3, discontinued SV ingestion earlier than TG patients (stage I), possibly because they were weaker or more sensitive to one or more of the factors listed above. No attempt was made to rank the importance of these factors. Because no prior. data on efficacy of using SV for different durations were available, all these patients were included in analyses to avoid bias.

Nonrandomized trials are recommended for phase II studies. Bias in patient selection can be minimized by using the same clinical entry criteria and prognostic factors for patients in the control and the study group. In the present study, tumor cell type, stage, previous and concurrent therapies, age, gender, KPS, and BMI in the CG and the SVG patients were comparable. KPS, change in body weight, and extent of disease are considered strong survival predictors for cancer patients. These prognostic indicators were comparable in the CG and the SVG patients at entry but rapidly declined in the CG patients. In contrast, they often improved or remained unchanged, or their decline was less rapid and severe in SVG patients. All these indicators improved or were unchanged in all TG patients. Thus, ingestion of SV was associated with maintenance or improvement in KPS and body weight.

The median survival time of the CG patients was within the expected historical range. Median survival time and mean survival were significantly longer for SVG than for CG patients. For changes of KPS and body weight, each patient was used as his own control. These changes within individual patients are not affected by the difference between patients or by the number of patients and are strong prognostic indicators for patient survival. The rapid declines in these survival indicators in the CG but not in the SVG patients are consistent with the observed survival difference between the two groups.

Quality of life and avoidance of drug toxicity, cachexia, and recurrent and metastatic disease remain important challenges in the treatment of NSCLC. In the 24-month study period, no detectable toxicity occurred in the five stage I patients, and their KPS and body weight also improved. Moreover, although recurrent tumor in stage I NSCLC patients is a major cause of death, all five stage I TG patients had no recurrent tumor in the two-year study period. They all had primary radiotherapy, and one also had surgery. Their 24-month recurrence-free survival compares favorably with the 59% recurrence rate and the 52% death rate due to lung cancer in two years for stage I NSCLC patients treated with radiotherapy alone or the 35% two-year recurrence rate of stage I NSCLC patients treated with surgery alone.

The apparent benefit of SV may be due to one or more antitumor components in SV (Table 1). The antitumor effect of purified forms of β-glucans has been well documented and is host mediated. Soybeans contain various antitumor components, e.g., protease inhibitors, saponins, inositol hexaphosphate, genistein, and other phytoestrogens. Moreover, NSCLC is an immune-suppressing disease, and immunosuppressive factors produced by NSCLC cells have been well characterized. Further investigations of the benefits of SV and other combinations of foods containing different antitumor and immune-enhancing entities for cancer patients are warranted. This approach is attractive because of its simplicity, low cost, and lack of toxicity.

This study indicates that the daily ingestion of SV is safe, nontoxic, and well tolerated by NSCLC patient at all stages. The prolonged survival of stage III/IV NSCLC patients observed in this phase I/II study is noteworthy and warrants further large, placebo-controlled, randomized studies. Given the high incidence and poor prognosis of lung cancer, modest improvements in survival can be translated into many thousands of useful added years for NSCLC patients.

Furthermore, strong Antitumor efficacy of SV was also observed in 2 tumor models in mice, namely, lung carcinoma Line I in BALB/c mice and Sarcoma S1509a in A/J(H-2a) mice (2,3).

EXAMPLE 2

Colon Cancer

Subsequently, a Czech patient with stage IV colon cancer had an unusually prolonged survival (>4 years) with conventional therapies and daily ingestion of SV.

Four sets of CT scans were taken on the following dates: Oct. 13, 1986, Nov. 11, 1986, Nov. 26, 1986, and Feb. 10, 1987. Three intracranial enhancing lesions (FIGS. 2A, 2B, and 2C) were identified; their transverse directions were measured (in mm).

Figure 2A:
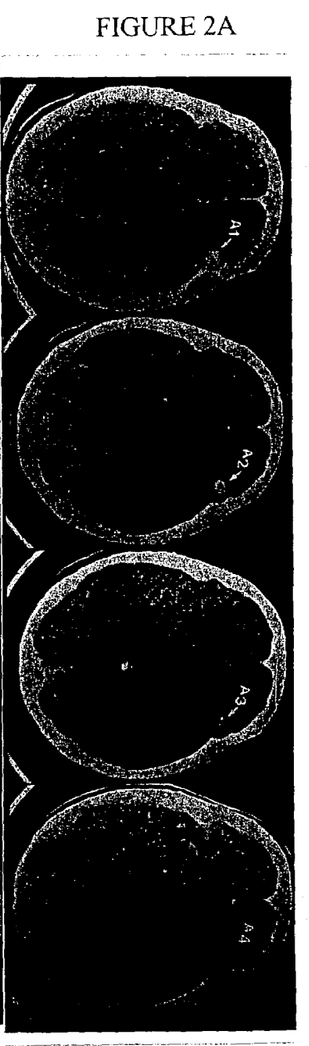
FIG. 2 is a CT scan of three metastatic brain lesions illustrating their disappearances after the SV treatment.

In FIG. 2A, the lesion, located in the left posterio-lateral middle frontal gyrus, was surrounded by edema anteriorly and medially. No obvious focal indentation, deformity, or shift of the ventricular system was observed. The lesion measured 13 mm (A1); 13.6 mm (A2); 8.6 mm (A3); no clear cut enhancing mass lesion was identified in the area (A4). The edema represented by areas of low density shows marked diminution. Unlike the first, second, and third CT scans, where the lesions are still clearly seen, the last CT scan was taken with a higher quality scanner (GE 9800 scanner). Therefore, even a small enhancing lesion, if still present, should be better demonstrated.

Figure 2B:
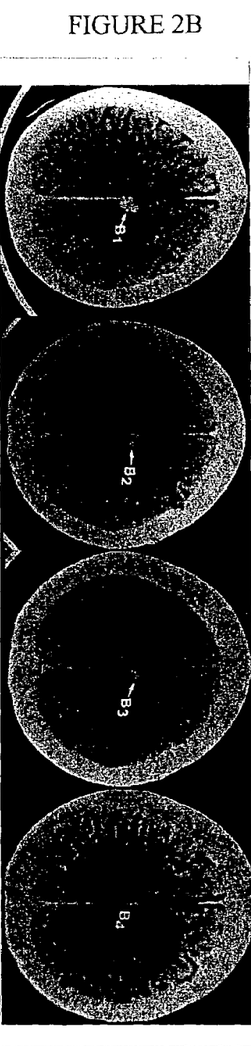

In FIG. 2B, the lesion, located in the medial aspect of the precentral gyrus on the left side immediately adjacent to the falx, measured 7.7 mm (B1); 11.5 mm (B2); 6.7 mm (B3); no clear cut enhancing mass lesion was identified in the area (B4).

Figure 2C:
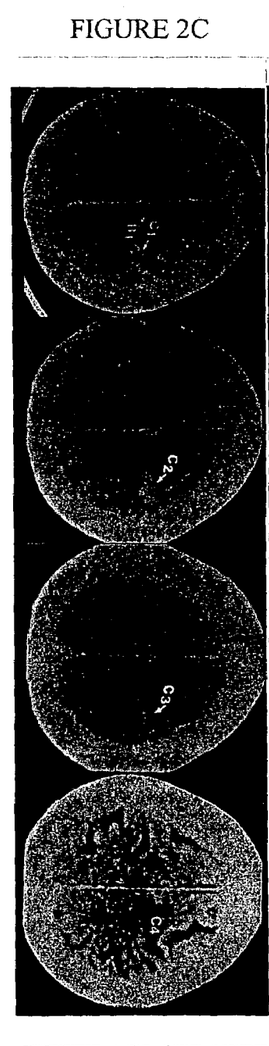

In FIG. 2C, the lesion was located in the precentral gyrus (upper convexity side). A moderate degree of edema was seen involving the white matter of the high frontoparietal lobe. The pre- and postcentral gyri were widened and the adjacent sulci were narrowed. This lesion measured 11.5 mm (C1); 12.1 mm (C2); 6.0 mm (C3); no clear cut enhancing mass lesion was identified in the area (C4).

EXAMPLE 3

AIDS Treatment

An AIDS patient was administered SV when his $CD4^+$ decreased to a dangerously low level (95 cells/mm$^3$) condition deteriorated, and had multiple infections. After ingesting SV for 2 months, not only his health improved to normal level, his $CD4^+$ cell count also increased to normal level, namely, to 475 in 2 months and over 600 in 6 months. This patient did not receive any other treatment except for daily ingestion of SV during this time. Thus, the change in his $CD4^+$ cell count and health condition after ingesting SV alone is considered an objective response to SV.

The invention claimed is:

1. A method of enhancing an immune function comprising
    a) identifying a subject who is immunosuppressed; and
    b) administering to said identified subject an immune function enhancing effective amount of a dietary supplement comprising soybean, mushroom, mung bean, red date, scallion, garlic, lentil bean, leek, hawthorn fruit, onion, ginseng, angelica root, licorice, dandelion root, senegal root, ginger, olive, sesame seed, and parsley, or extracts thereof, administered periodically for a time to achieve improved immune function in comparison to said subject that was not administered said dietary supplement,
    wherein said improved immune function results in increased CD4+ cell levels.

2. The method defined in claim 1 wherein the extract is a boiling water extract.

3. The method defined in claim 1 wherein the soybean, mushroom and mung beans are present in similar amounts.

4. The method defined in claim 1 wherein the soybean, mushroom, and mung bean, or extracts thereof contain at least one phytoestrogen, at least one β-glucan, at least one saponin, inositol hexaphosphate, and at least one lectin.

5. The method defined in claim 4 wherein the at least one phytoestrogen is at least one member selected from the group consisting of genistein, coumestrol, daidzein, and biochanin A;
    the at least one β-glucan is at least one member selected from the group consisting of lentinan, pachymaran, zymosan, schizophyllan, KS-2, and pachyman; and
    the at least one lectin is at least one member selected from the group consisting of phytohemagglutinin and concanavalin A.

6. The method defined in claim 5 wherein at least one phytoestrogen is genistein, biochanin A or coumestrol.

7. The method defined in claim 4, wherein the phytoestrogen is genistein.

8. The method defined in claim 1 wherein the dietary supplement consists essentially of soybean, mushroom, mung bean, red date, scallion, garlic, lentil bean, leek, hawthorn fruit, onion, ginseng, angelica root, licorice, dandelion root, senegal root, ginger, olive, sesame seed, and parsley.

9. The method defined in claim 1 wherein the dietary supplement consists of soybean, mushroom, mung bean, red date, scallion, garlic, lentil bean, leek, hawthorn fruit, onion, ginseng, angelica root, licorice, dandelion root, senegal root, ginger, olive, sesame seed, and parsley.

* * * * *